United States Patent [19]
Bray et al.

[11] Patent Number: 5,512,256
[45] Date of Patent: Apr. 30, 1996

[54] METHOD OF SEPARATION OF YTTRIUM-90 FROM STRONTIUM-90

[75] Inventors: Lane A. Bray; Dennis W. Wester, both of Richland, Wash.

[73] Assignee: Battelle Memorial Institute, Richland, Wash.

[21] Appl. No.: 267,649

[22] Filed: Jun. 29, 1994

Related U.S. Application Data

[63] Continuation-in-part of Ser. No. 58,901, May 6, 1993, abandoned, which is a continuation-in-part of Ser. No. 880,961, May 8, 1992, abandoned.

[51] Int. Cl.$^6$ .................................................. C01F 1/00
[52] U.S. Cl. .................................................. 423/2
[58] Field of Search ........................................ 423/2

[56] References Cited

U.S. PATENT DOCUMENTS 3,122,414   2/1964   Horner et al. .................... 423/2

OTHER PUBLICATIONS

J. A. Partridge and R. C. Jensen; "Purification of Di–(2–ethylhexyl)phosphoric Acid by Precipitation of Copper(II) Di–(2–ethylhexl) phosphate"; J. Inorg. Nucl. Chem., 1969, vol. 31, pp. 2587–2589, Pergamon Press.

J. S. Wike, C. E. Guyer, D. W. Ramey, and B. P. Phillips (Chemical Technology Division, Oak Ridge National Laboratory); "Chemistry for Commercial Scale Production of Yttrium–90 for Medical Research"; Journal of Appl. Radiat. Isot., vol. 41, No. 9, pp. 861–865, 1990.

Te–Wei Lee, Gann Ting; Institute of Nuclear Energy Research, Atomic Energy Council, Taiwan, R.O.C.; "Study on the Separation of Carrier–Free Yttrium–90 from Strontium–90", Isotopenpraxis 27 (1991) 6, pp. 269–273.

L. A. Bray (Fission Product Chemistry, Chemistry Department, Battelle–Northwest, Pacific Northwest Laboratory); "Purification of Strontium–90 from Magnesium"; BNWL–46, Mar. 15, 1965.

Primary Examiner—Ngoclan Mai
Attorney, Agent, or Firm—Paul W. Zimmerman

[57] ABSTRACT

A method for purifying Y-90 from a Sr-90/Y-90 "cow" wherein raw Sr-90/Y-90 source containing impurities is obtained from nuclear material reprocessing. Raw Sr-90/Y-90 source is purified to a fresh Sr-90/Y-90 source "cow" by removing impurities by addition of sodium hydroxide and by removing Cs-137 by further addition of sodium carbonate. The "cow" is set aside to allow ingrowth. An HDEHP organic extractant is obtained from a commercial supplier and further purified by saturation with Cu(II), precipitation with acetone, and washing with nitric acid. The "cow" is then dissolved in nitric acid and the purified HDEHP is washed with nitric acid and scrubbed with either nitric or hydrochloric acid. The dissolved "cow" and scrubbed HDEHP are combined in an organic extraction, separating Y-90 from Sr-90, resulting in a Sr-90/Y-90 concentration ratio of not more than 10(E-7), and a metal impurity concentration of not more than 10 ppm per curie of Y-90. The separated Y-90 may then be prepared for delivery.

10 Claims, 1 Drawing Sheet

METHOD OF SEPARATION OF YTTRIUM-90 FROM STRONTIUM-90

This invention was made with Government support under Contract DE-AC06-76RLO 1830 awarded by the U.S. Department of Energy. The Government has certain rights in the invention.

This application is a Continuation-In-Part of U.S. patent application Ser. No. 08/058 901 filed May 6, 1993 now abandoned, which is a Continuation-In-Part of U.S. patent application, Ser. No. 07/880,961, filed May 8, 1992, now abandoned.

FIELD OF THE INVENTION

The present invention relates generally to a method for separating Yttrium-90 (Y-90) from Strontium-90 (Sr-90) and further purifying the Y-90 for applications including but not limited to cancer research and treatment.

BACKGROUND OF THE INVENTION

Yttrium-90 with a half-life of 64 hours is finding increasing use in the treatment of various forms of cancer. The National Cancer Institute has listed Y-90 as one of the top three radioactive isotopes being evaluated for use in cancer therapy. Medical researchers studying cancer treatment for the past five years have developed techniques using radioactive Y-90 labeled monoclonal antibodies to treat fatal adult T-cell leukemia. Others are using Y-90 labeled antibodies for studies of tumor therapy of ovarian, colon, and lymphatic cancers.

In order to be useful, the Y-90 must be exceptionally pure; free from other metal ions and free from Sr-90, an extremely toxic bone-seeking isotope. The typical therapeutic dose of Y-90 labeled monoclonal antibodies is the range of 100–300 millicuries of Y-90 per patient. Since an antibody is modified to contain only one molecule of chelating ligand per molecule of immunoprotein within the antibody, the total binding sites for metal ions are limited to about 7(10E-9) moles on 1 mg of chelate-modified immunoprotein. Since complexes of several metal ions including but not limited to zirconium(IV) and iron(III) form much stronger bonds than Y-90, specifications for chemical purity of Y-90 are necessarily strict for efficient labeling. (J. S. Wike et al. (Appl. Radiat. Isot. Vol. 41, No. 9, pp 861–865, Int. J. Radiat. Appl. Instrum. Part A, 1990, CHEMISTRY FOR COMMERCIAL SCALE PRODUCTION OF YTTRIUM-90 FOR MEDICAL RESEARCH), report producing multi-curie quantities of Y-90 having Sr-90/Y-90 separation factors of about 2(10E-6).

With the increased demand for Y-90, there is a need for a method capable of producing multi-curie quantities of Y-90 on a weekly basis with purities in terms of Sr-90/Y-90 separation factors less than 1(10E-8), and chemical impurities of unwanted cations including but not limited to iron, nickel, or a combination, wherein the chemical impurities are less than 10 ppm (parts per million) per curie of Y-90.

SUMMARY OF THE INVENTION

The present invention relates generally to a method for separating Y-90 from Sr-90 and further purifying the Y-90 for applications including but not limited to cancer research and treatment. More specifically, the present invention relates to the preparation of ultra pure Y-90 through the use of high purity Sr-90 as a source together with high purity reagent process chemicals. More specifically, the invention is characterized by the following three elements: (1) instead of using commercial di(2-ethylhexyl)phosphoric acid (HDEHP) that is acid washed as an organic extractant for separating Y-90 from Sr-90, a highly purified HDEHP is prepared according to purification steps taught by Partridge and Jensen, PURIFICATION OF DI-(2-ETHYLHEXYL) PHOSPHORIC ACID BY PRECIPITATION OF COPPER(II) DI-(2-ETHYLHEXYLPHOSPHATE, Journal of Inorganic Nuclear Chemistry, 1969, Vol 31. pp 2587–2589, Pergamon Press, 1969; (2) highly purified nitric acid supplied as Ultrex is used instead of hydrochloric acid; and (3) removing traces of organic extractant from the aqueous product contained in nitric acid with hexane instead of the classical fuming method using a mixture of nitric and hydrochloric acids.

The subject matter of the present invention is particularly pointed out and distinctly claimed in the concluding portion of this specification. However, both the organization and method of operation, together with further advantages and objects thereof, may best be understood by reference to the following description.

DESCRIPTION OF THE PREFERRED EMBODIMENT(S)

Figure 1:
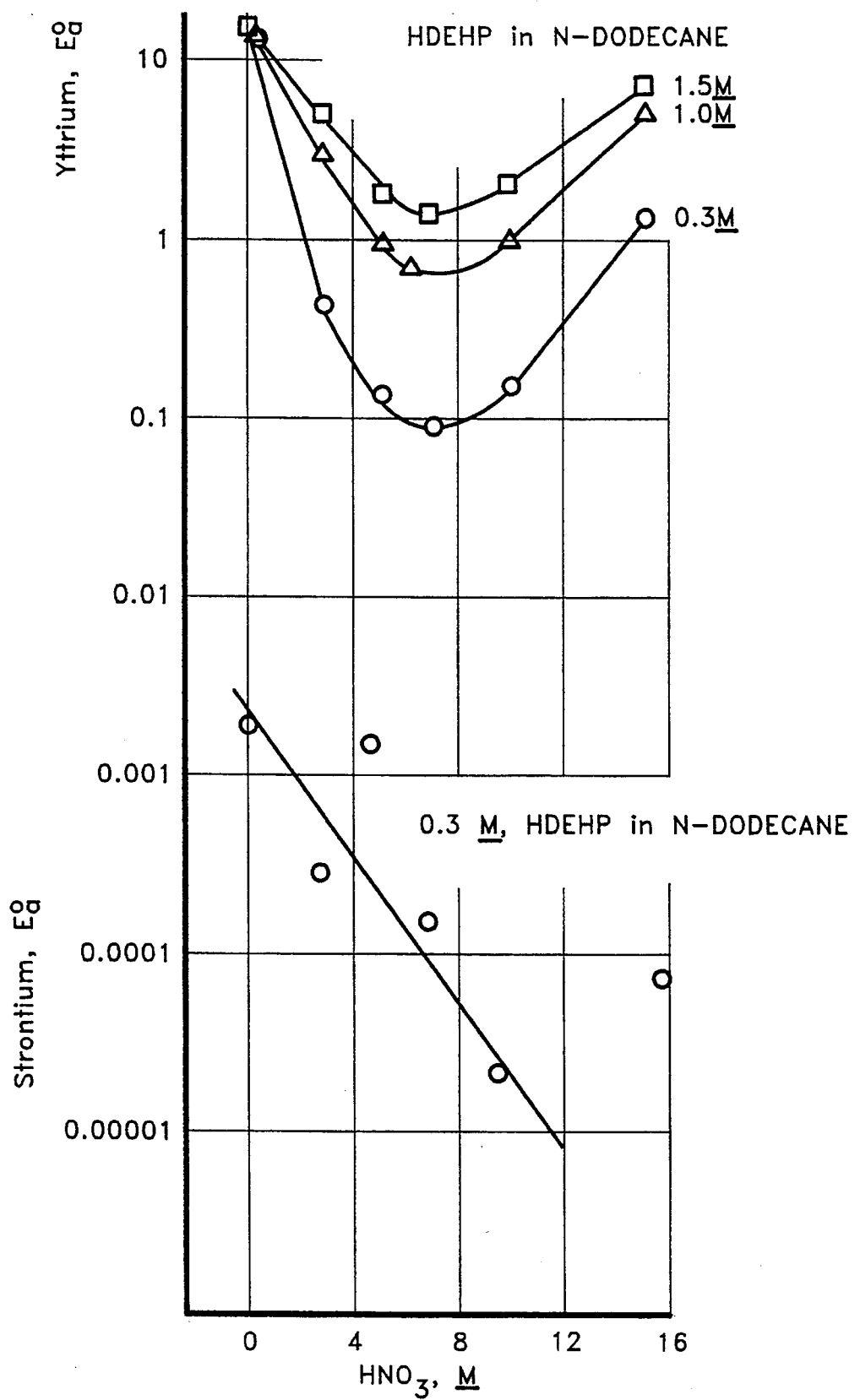
FIG. 1 is a graph of chemical equilibrium constants for Y-90 and Sr-90 in nitric acid and di(2-ethylhexyl)phosphoric acid (HDEHP) diluted with n-dodecane.

The present invention is a method for purifying Y-90, by separating Y-90 from a source mixture of Sr-90 and Y-90 primarily by solvent extraction of the Y-90 into a dilute organic solution of highly purified di(2-ethylhexyl) phosphoric acid (HDEHP) in a diluent of n-dodecane. Yttrium-90 can be effectively extracted into an organic phase in dilute nitric acid (~0.3M). As shown in FIG. 1, a single-stage separation of Y-90 from Sr-90 based on an equilibrium constant for Y-90 of 10 and an equilibrium constant for Sr-90 of 0.001 achieves a Sr-90/Y-90 separation ratio in the organic phase of 1(10E-4). Further Sr-90 removal to achieve separation ratios at or below 1(10E-8) is accomplished by washing the Y-90 organic phase with dilute nitric acid (~0.3M $HNO_3$).

Achieving separation ratios at or below 1(10E-8) is done in the present invention by applying two criteria. The first criteria is limiting the amount of impurities introduced into the processing by selecting highly purified reagents and by purifying the reactants prior to use. The second criteria is carefully selecting the type and order of processing steps. The processing steps include:

(1) purifying a raw Sr-90/Y-90 source and ingrowth, (2) purifying an HDEHP organic extractant, (3) pretreatment of fresh Sr-90/Y-90 source and purified organic extractant, (4) organic extraction separation of Y-90 from Sr-90, and (5) Y-90 product treatment.

The reactants are a fresh Sr-90/Y-90 source or "cow" (1–2 curies) in a solution of nitric acid, preferably about 0.3M nitric acid, and a highly purified organic extractant of HDEHP in n-dodecane, preferably about 0.3M HDEHP.

PURIFYING A RAW STRONTIUM-90/YTTRIUM-90 SOURCE AND INGROWTH

Raw Sr-90/Y-90 source may be obtained as a by-product from nuclear waste reprocessing. When obtained in this way, the raw Sr-90/Y-90 source also contains at least a first group of ionic impurities including iron, magnesium, calcium, sodium, chromium and cerium. Purification of raw Sr-90/Y-90 is generally described in PURIFICATION OF STRONTIUM-90 FROM MAGNESIUM, L. A. Bray, BNWL-46, UC-70, Mar. 15, 1965, but because the raw Sr-90/Y-90 source used in that report did not contain cesium-137 (Cs-137), modification of the purification process described therein is necessary for the present invention.

Raw Sr-90/Y-90 source containing Cs-137 in addition to the first group of impurities, is obtained as a by-product of nuclear waste reprocessing. Separation of the impurities is accomplished by first removing any and all ionic impurities except the Cs-137, then secondly removing the Cs-137. In a preferred method, the first group of ionic impurities are removed by adding sodium hydroxide to raw Sr-90/Y-90 source. Sufficient sodium hydroxide is added to obtain a pH between about 10 to about 12. It is preferred that the sodium hydroxide contain no or undetectable amounts of carbonate. The first group of ionic impurities precipitates with the sodium hydroxide forming hydroxide solids. The solids are removed by filtering, leaving an intermediate solution of Sr-90 and Cs-137. Sodium carbonate is added to the intermediate solution to form a precipitate with the Sr-90, leaving the Cs-137 in solution. It is preferred that the amount of sodium carbonate is sufficient to bring the intermediate solution to a concentration of about 0.15M sodium carbonate. The Sr-90 precipitate is then filtered and washed with dilute sodium carbonate for removing remaining traces of Cs-137. It is preferred that the dilute sodium carbonate be in an amount of about 10 mL, having a concentration of from about 0.1M to about 0.2M. After washing, the Sr-90 is dried as a "cow" for storage and ingrowth of Y-90.

The "cow" is set aside to allow time for ingrowth, i.e., decay of a portion of Sr-90 (half-life of 30 years) to Y-90 (half-life of 64 hours). The amount of time is preferably from about 1 week to about 2 weeks providing ingrowth of maximum Y-90 radioactivity from about 80% to about 95%.

PURIFICATION OF HDEHP ORGANIC EXTRACTANT

In a preferred method, the organic extractant used to separate Sr-90 from Y-90 is obtained as reagent grade HDEHP, available from chemical suppliers; for example, Eastman, Catalog Number 8755 [$CH_3(CH_2)_3CH(C_2H_5)CH_2O$]POOH, then further purified from iron and other metals. Reagent grade HDEHP contains traces of metallic impurities including iron. Washing the HDEHP with hydrochloric acid or nitric acid removes most metallic impurities, but does not completely remove iron which is tightly held. Iron remaining in the HDEHP will slowly leach out of the HDEHP into a product solution during extraction, thereby leaving an iron impurity in the product solution. Therefore, the HDEHP used in the present invention is first purified by a method described by Partridge and Jensen (1965).

Purification of HDEHP begins with saturating an organic solution of HDEHP with copper(II) (Cu(II)). The concentration of HDEHP is preferably about 1M. The Cu(II) may be added either by adding freshly precipitated copper hydroxide, or by adding sodium hydroxide to a solution of copper sulfate in contact with the organic HDEHP phase. Preferred solvents include benzene, carbon tetrachloride, cyclohexane, diethyl ether, and methyl alcohol.

After saturating the HDEHP with Cu(II), a remaining aqueous phase is removed. Acetone is slowly added to precipitate a first precipitate, Cu(DEHP)2, leaving impurities including iron behind. It is preferred that the HDEHP with Cu(II) is stirred while the acetone is added. The first precipitate is then filtered, then washed with acetone, and air dried. Further purification may be obtained by redissolving the precipitate and adding acetone to obtain a second precipitate.

The first or second precipitate is converted back to HDEHP by washing the precipitate with a dilute aqueous acid. Partridge and Jensen suggest hydrochloric acid. The acid wash may be repeated until all Cu(II) is removed. The remaining aqueous acid is removed with water washes. Finally, the remaining water is removed with a rotating evaporator. The resulting concentration of purified HDEHP is about 3M.

PRETREATMENT OF FRESH STRONTIUM-90/YTTRIUM-90 SOURCE AND PURIFIED ORGANIC EXTRACTANT

After initial purification and ingrowth, the dried Sr-90/Y-90 source "cow" is adjusted to a volume equivalent to a volume of purified organic extractant by dissolving in nitric acid. An amount of nitric acid of from about 3 mL to about 10 mL, but preferably about 5 mL, is added to the "cow". Both the volume adjusted "cow" and the volume adjusted purified organic extractant are further concentration adjusted based upon FIG. 1 from about 0.25M to about 0.35M, but preferably about 0.3M, thereby producing a separation ready source.

The methods of purification and pretreatment of a raw Sr-90 source are appropriate for producing any amount of fresh Sr-90 source "cow" but it is preferable to produce from about 4 mL to about 10 mL of separation ready source.

The purified HDEHP organic extractant, diluted to 0.3M with n-dodecane, is acid washed to equilibrate the organic with acid and to produce about 5 mL of separation ready extractant. The purified HDEHP organic extractant is first washed twice with concentrated nitric acid of preferred concentrations ranging from about 7M to 10M, but most preferably about 7M. The concentrated acid washes are followed by two scrubs using dilute nitric acid. It is preferred that the dilute nitric acid have concentrations ranging from about 0.1M to about 0.3M, but is most preferably about 0.3M. Nitric acids are available in various grades, but it is preferred to use very pure nitric acids as obtainable from J. T. Baker, Inc. as ULTREX Ultrapure reagents. This pretreatment of the organic extractant results in a high-purity organic extractant containing no detectable iron. This is superior to that achieved by repeated washing with concentrated hydrochloric acid of commercial grade organic extractant as reported by Wike (1990).

ORGANIC EXTRACTION SEPARATION OF YTTRIUM-90 FROM STRONTIUM-90

After pretreatment, an amount of separation ready source "cow" is then contacted with about an equal amount of separation ready organic extractant for the solvent extraction step, wherein the amount is from about 3 mL to about 10 mL. The solvent extraction is carried out by contacting (using a glass-covered stir bar and magnetic stir motor) the separation ready organic extractant with the separation ready source for a time of from about 5 minutes (min.) to about 30 min., but preferably about 5 min., to allow the separation ready source to reach equilibrium with the separation ready organic extractant, thereby allowing the separation ready organic extractant to extract the Y-90 from the separation ready source mixture, leaving an organic phase containing Y-90 and an aqueous phase retaining Sr-90. Next, the organic phase containing Y-90, which is immiscible with the remaining aqueous Sr-90 phase, is allowed to separate for a time of from about 5 min. to about 30 min., but preferably about 5 min., to ensure thorough separation of organic and aqueous phases. Finally, the organic phase containing Y-90 (about 9 mL) is decanted from the remaining Sr-90.

At this point, the remaining Sr-90 is an aqueous Sr-90 source or "cow" having very little Y-90 and containing traces of organic extractant left from the decanting step. The aqueous Sr-90 "cow" is scrubbed twice using hexane. An amount of hexane from about 3 mL to about 6 mL, but preferably about 3 mL, is mixed with the aqueous Sr-90 "cow" to remove traces of the organic extractant. After removal of the second hexane scrub, the aqueous Sr-90 "cow" is dried to remove any remaining hexane. After drying, the Sr-90 "cow" is ready for storage and ingrowth of Y-90. Hexane is available in various grades, but it is preferred to use very pure hexane as obtainable from chemical suppliers; for example, Spectro Grade Hexanes, Reagent ACS, Catalog No. 170034.

Proceeding with obtaining purified Y-90, the organic extractant (about 5 mL) contains Y-90 and traces of Sr-90 impurity. Purified Y-90 product is obtained in three steps, (1) at least two nitric acid scrubs, (2) at least one acid strip, and (3) at least one hexane scrub. A fourth step, at least one boildown to dryness, is optional depending upon the type of acid strip.

In a preferred method, the organic extractant is scrubbed two or three times with dilute nitric acid. Each nitric acid scrub comprises mixing approximately equal volumes of organic extractant containing Y-90 and dilute nitric acid, wherein the volumes may range from about 3 mL to about 5 mL, but preferably are about 5 mL, having a preferred concentration of about 0.3M. The nitric acid is mixed with the organic extractant for a time from about 5 min. to about 30 min., but with 5 min. preferred. It is further preferred to stir the mixture during this time with a magnetic stirrer and a glass-covered stir bar. Between each scrub and after the last scrub, the mixture is allowed to separate into organic and aqueous phases for a time from about 5 min. to about 15 min., with 5 min. preferred. The aqueous phase containing traces of Sr-90 impurity is removed.

The scrubbed organic extractant containing the Y-90 product is further subjected to one to three acid strips. Each acid strip comprises mixing approximately equal volumes of scrubbed organic extractant containing Y-90 and concentrated acid, wherein the volumes may range from about 5 mL to about 9 mL, but preferably about 5 mL. When stripping with nitric acid, the concentration of concentrated acid can be from about 5M to about 9M, but is preferably about 7M. When stripping with hydrochloric acid, the concentration of the concentrated acid can be from about 6M to about 10M, but is preferably about 8M. Between each strip and after the last strip, the mixture is allowed to separate into organic and aqueous phases for a time from about 5 min. to about 15 min., with 5 min. preferred. The aqueous phase containing Y-90 is collected.

The aqueous phase containing Y-90 is then mixed with one to three hexane scrubs to further remove traces of organic extractant from the Y-90. The amount of hexane is preferred to be about 5 mL for about 10 mL of stripped product. For a volume of about 9 mL of stripped Y-90, the amount of hexane may range from about 3 mL to about 9 mL. With lesser amounts of hexane, more scrubs are needed. Hexane may be in contact with the Y-90 for times ranging from about 5 min. to about 30 min., but it is preferred that the contact time is about 5 min.

When hydrochloric acid is used for scrubbing, after the hexane scrubs, the remaining solution is the Y-90 product solution. The product solution may be placed in a V-bottom vial.

When nitric acid is used for scrubbing, after the hexane scrubs, the remaining Y-90 nitric acid solution is boiled to dryness. Boiling may be done in any container, but is preferably done in a closed container, preferably a plastic tube, and most preferably a polytetrafluroethylene (e.g., Teflon) tube.

The dried Y-90 product may be further placed back in solution according to end-use specifications.

The dry product may be dissolved into solution by adding concentrated hydrochloric acid to the dry product while it is hot. The amount of hydrochloric acid may be from about 0.1 mL to about 1 mL, but preferably about 0.3 mL of a concentration from about 7M to about 10M, but most preferably about 8M. One or two, preferably two, additional volumes of about 0.8M hydrochloric acid are used to wash the Y-90 product from the heating container (Teflon tube) into a collection container, preferably a V-bottom vial. Hydrochloric acids are available in various grades, but it is preferred to use very pure hydrochloric acids as obtainable from J. T. Baker, Inc., as ULTREX Ultrapure reagents.

YTTRIUM-90 PRODUCT TREATMENT

At this point, the product solution in the V-bottom vial may be treated for delivery in one of two product treatments. In a first product treatment, the product may be dried then brought into a customer specified hydrochloric acid solution concentration (usually about 0.05M HCl), or in a second product treatment the product may be passed through an ion exchange then dried and put into a hydrochloric acid solution concentration (of customer choice).

In the first product treatment, the Y-90 product is dried then dissolved in hydrochloric acid. The amount of hydrochloric acid may range from about 0.1 mL to about 1.0 mL, and the concentration of hydrochloric acid may range from about 0.05M to about 1.0M, but is preferably about 0.05M.

In the second product treatment, the Y-90 product is dried and dissolved in hydrochloric acid. The amount of hydrochloric acid may range from about 0.3 mL to about 1.0 mL, preferably about 0.5 mL, and the concentration of hydrochloric acid may range from about 7M to about 9M, but is preferably about 7M.

The hydrochloric acid containing Y-90 is transferred to an ion-exchange column for removal of any traces of iron (and other metals). The ion-exchange column contains an amount of resin from about 100 mg to about 400 mg, but preferably about 140 mg. The preferred ion-exchange resin is chloride form anion-exchange resin, and more preferably an AG-1, 4X, 200–400 mesh ion-exchange resin or equivalent available from Bio-Rad. After the ion exchange, the resin is washed one or two times with hydrochloric acid of about 7M in an amount of about 0.5 mL.

After the ion-exchange and washing, the hydrochloric acid containing Y-90 is dried by heating. While the dry Y-90 is hot, an amount of dilute hydrochloric acid is added where the amount is from about 0.1 mL to about 1.0 mL, having a concentration from about 0.05M to about 0.3M, but preferably about 0.05M. Heating is continued for a time from about 5 min. to about 30 min., but preferably about 15 min. to bring the dry Y-90 product into solution.

Customer-specified hydrochloric acid containing Y-90 solutions have been analyzed and found to have separation ratios of Sr-90 to Y-90 from 10(E-9) to 10(E-6), with an average of 10(E-8) for about 20 batches. Analytical results further show concentrations of competing metals including but not limited to iron, calcium, and zinc of 0–5 ppm iron, 0–5 ppm calcium, and 0–5 ppm zinc, respectively, at 1 Ci Y-90/mL.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for purifying Y-90, comprising steps of:
   (a) purifying a raw Sr-90/Y-90 source to a fresh Sr-90 source "cow" and permitting Y-90 ingrowth by removing at least a first group of impurities including iron, calcium, magnesium, sodium, chromium, and cerium by precipitating said impurities with sodium hydroxide wherein the sodium hydroxide contains little or no carbonate, and further purifying said "cow" by adding sodium carbonate for precipitating Sr-90 and leaving Cs-137 in solution,
   (b) purifying a HDEHP organic extractant to remove traces of metal impurities,
   (c) pretreating of said "cow" to a separation ready Sr-90/Y-90 source,
   (d) pretreating purified organic extractant to a separation ready organic extractant, and
   (e) separating Y-90 from Sr-90 by mixing said separation ready Sr-90/Y-90 source with said separation ready organic extractant obtaining a Y-90 product that has a Sr-90/Y-90 concentration ratio of not more than 10(E-7), and a metal impurity concentration not more than 10 ppm per curie of Y-90.

2. A method as recited in claim 1, wherein pretreating of said "cow" to a separation ready Sr-90/Y-90 source, comprises a step of:
   (g) dissolving said "cow" in nitric acid.

3. A method as recited in claim 1, wherein pretreating purified organic extractant to a separation ready organic extractant, comprises the steps of:
   (h) washing said purified organic extractant with concentrated nitric acid, and
   (i) scrubbing the washed purified organic extractant with dilute nitric acid.

4. A method as recited in claim 1, wherein separating Y-90 from Sr-90 comprises steps of:
   (j) mixing said separation ready Sr-90/Y-90 source with said separation ready organic extractant, thereby extracting Y-90 from the source into the extractant, the extractant receiving a trace amount of Sr-90,
   (k) scrubbing the mixture of step (j) with an amount of dilute high purity nitric acid reagent for further removal of the trace amount of Sr-90,
   (l) stripping Y-90 from the scrubbed mixture of step (k) with a concentrated high purity acid reagent solution, and
   (m) removing traces of organic extractant from the stripped Y-90 of step (l) with hexane.

5. The method as recited in claim 4, wherein the concentrated high purity acid reagent solution is hydrochloric acid.

6. The method as recited in claim 4, wherein the concentrated high purity acid reagent solution is nitric acid.

7. The method as recited in claim 4, further comprising the step of:
   (n) boiling the result of step (m) and obtaining a dry product of Y-90.

8. A method for purifying Y-90, comprising steps of:
   (a) procuring high purity nitric acid and hexane, reagents,
   (b) purifying a raw Sr-90/Y-90 source to a fresh Sr-90 source "cow" having at least 99.99 (weight or mole) percent chemical and radiochemical purity,
   (c) allowing a grow-in time for the purified fresh Sr-90 source to decay into a source mixture of Sr-90 and Y-90,
   (d) purifying an organic extractant with Cu(II) and acetone,
   (e) mixing a high purity dilute nitric acid reagent with the "cow" for pretreating said "cow" to a separation ready Sr-90/Y-90 sources,
   (f) pre-treating said purified organic extractant of step (d) reagent with a high purity nitric acid reagent washing, to a separation ready organic extractant,
   (g) combining the pre-treated mixture of step (e) with the separation ready organic extractant of step (f) for solvent extraction of Y-90 into an organic phase,
   (h) scrubbing the organic phase of step (g) with an amount of dilute high purity nitric acid reagent for further removal of trace amounts of Sr-90,
   (i) stripping Y-90 from the scrubbed organic phase of step (h) with a concentrated high purity acid reagent solution,
   (j) removing traces of the organic phase from the stripped Y-90 of step (i) with hexane,
   (k) boiling the result of step (j), and obtaining a first dry product of Y-90 having a Sr-90/Y-90 concentration ratio of not more than 10(E-7), and a metal impurity concentration of not more than 10 ppm per curie of Y-90,
   (l) dissolving the first dry product in concentrated hydrochloric acid,
   (m) removing trace metals from the dissolved first dry product through ion exchange,
   (n) heating the dissolved first dry product of step (m) making, a second dry product and
   (o) dissolving the second dry product in dilute hydrochloric acid.

9. The method as recited in claim 8, wherein the concentrated high purity acid reagent solution is hydrochloric acid.

10. The method as recited in claim 8, wherein the concentrated high purity acid reagent solution is nitric acid.

* * * * *